United States Patent [19]

Bollinger et al.

[11] 4,124,375

[45] Nov. 7, 1978

[54] SUBSTITUTED PHTHALIMIDES FOR REGULATING THE GROWTH OF PLANTS

[75] Inventors: Frederic G. Bollinger; John J. D'Amico, both of St. Louis; Dale J. Hansen, St. Charles, all of Mo.

[73] Assignee: Monsanto Company, St. Louis, Mo.

[21] Appl. No.: 841,425

[22] Filed: Oct. 12, 1977

[51] Int. Cl.² ............................................. A01N 5/00
[52] U.S. Cl. ..................................................... 71/96
[58] Field of Search .......................................... 71/96

[56] References Cited

U.S. PATENT DOCUMENTS 3,658,892 4/1972 Martin et al. ..................... 260/518 A

OTHER PUBLICATIONS

Hoffman et al., Science, vol. 109 (1949), p. 588.

*Primary Examiner*—Catherine L Mills
*Attorney, Agent, or Firm*—Richard H. Shear; Donald W. Peterson

[57] ABSTRACT

Certain substituted phthalimides have been found to be effective in regulating the growth of corn plants.

4 Claims, No Drawings

SUBSTITUTED PHTHALIMIDES FOR REGULATING THE GROWTH OF PLANTS

This invention relates to the use of certain phthalimides to regulate the growth of corn plants. More specifically, the phthalimides of the invention have been found to be effective in altering the sexual reproduction of such plants. Compounds 1-26 listed below are especially useful in inhibiting tassel development of corn plants.

| Compound No. | |
|---|---|
| (1) | N-(3-trifluoromethyl-4-nitrophenyl)phthalimide |
| (2) | N-(2-trifluoromethyl-5-bromophenyl)phthalimide |
| (3) | N-(3,5-dimethoxyphenyl)phthalimide |
| (4) | N-(3,4-dimethoxyphenyl)phthalimide |
| (5) | N-(4-pyridyl)phthalimide |
| (6) | N-(4,6-dimethyl-2-pyridyl)phthalimide |
| (7) | N-(3,5-dichloro-2-pyridyl)phthalimide |
| (8) | N-(6-methoxy-3-pyridyl)phthalimide |
| (9) | N-(4-methylphenyl)phthalimide |
| (10) | N-(3-mercaptophenyl)phthalimide |
| (11) | N-(2-fluorophenyl)phthalimide |
| (12) | 2-(p-phthalimidophenylthio)acetic acid |
| (13) | N-(3-trifluoromethyl-4-methoxyphenyl)phthalimide |
| (14) | N-(2-methyl-4-bromo-5-chlorophenyl)phthalimide |
| (15) | N-[m-(1-hydroxyethyl)phenyl]phthalimide |
| (16) | N-(3-trifluoromethyl-4-chlorophenyl)phthalimide |
| (17) | N-(2-chloro-5-trifluoromethylphenyl)phthalimide |
| (18) | N-(2-trifluoromethyl-4-chlorophenyl)phthalimide |
| (19) | N-(5-chloro-2-pyridyl)phthalimide |
| (20) | N-(3,5-dichlorophenyl)phthalimide |
| (21) | N-(4-chlorophenyl)phthalimide |
| (22) | N-(m-fluorobenzyl)phthalimide |
| (23) | N-(p-fluoroanilinomethyl)phthalimide |
| (24) | N-(phenylthiomethyl)phthalimide |
| (25) | m-phthalimidophenyl methylcarbamate |
| (26) | N-(2-nitro-4-trifluoromethylphenyl)phthalimide |

The compounds of the invention may be prepared in accordance with the following procedures:

Procedure A

A stirred charge containing 14.8 grams (0.1 moles) of phthalic anhydride, 1 gram of p-toluene sulfonic acid, 0.1 moles of the appropriate substituted aniline or aminopyridine and 200 ml of o-dichlorobenzene is heated at 180°–190° C. for six hours. During this heating period, 1.8 ml of water and 125 ml of o-dichlorobenzene are removed via a Dean Stark condenser. After allowing to cool to room temperature, 100 ml of heptane is added and stirring continued at 25°–30° C. for 30 minutes. The solid is collected by filtration and air-dried at 25°–30° C.

Procedure B

To a stirred solution at 140° C. containing 29.6 grams (0.2 moles) of phthalic anhydride in 200 grams of Varsol #2 (mixture of aromatic and aliphatic hydrocarbons), 0.2 moles of the appropriate substituted aniline is added in one portion. The stirred reaction mixture is heated at 140°–180° C. for 1.5 hours. During this heating period, 3.6 ml of water is removed by means of a Dean Stark condenser. After cooling to 100° C., 200 ml of heptane is added and stirring continued at 25°–30° C. for 30 minutes. The solid is collected by filtration and air-dried at 25°–30° C.

Procedure C

To a stirred slurry containing 29.6 grams (0.2 moles) of phthalic anhydride and 100 ml of acetic acid, 0.1 moles of the appropriate substituted aniline or aminopyridine is added in one portion. After heating at reflux for 2 hours, the stirred reaction mixture is allowed to cool to room temperature. After the addition of 800 ml of cold water, the reaction mixture is stirred at 0°–10° C. for 30 minutes. The solid is collected by filtration, washed with water until the washings are neutral to litmus and air-dried at 25°–30° C.

Compounds 1-21 have been prepared in accordance with the above procedures. Table I, below, summarizes the procedure used as well as the analysis obtained.

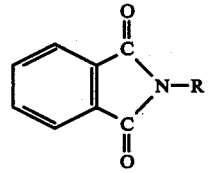

| Ex. # | Procedure | R | m.p. ° C. | Percent Yield | Percent C Calc'd. | Percent C Found | Percent H Calc'd. | Percent H Found | Percent N Calc'd. | Percent N Found | Percent F Calc'd. | Percent F Found |
|---|---|---|---|---|---|---|---|---|---|---|---|---|
| 1 | A | -C₆H₃(CF₃)(NO₂) | 159-61[a] | Theor. | — | — | — | — | 8.33 | 8.36 | 16.95 | 16.79 |
| 2 | A | -C₆H₃(F₃C)(Br) | 135-6[a] | 73 | — | — | — | — | 3.78 | 3.86 | 15.40 | 15.55 |
| 3 | A | -C₆H₃(OCH₃)(OCH₃) | 202-3[b] | 99 | 67.83 | 67.59 | 4.62 | 4.74 | 4.94 | 4.72 | — | — |
| 4 | A | -C₆H₃(OCH₃)(OCH₃) | 210-11[c] | 99 | 67.83 | 67.86 | 4.62 | 4.72 | 4.94 | 4.80 | — | — |

-continued

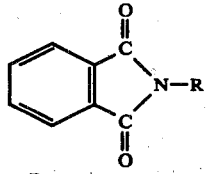

| Ex. # | Procedure | R | m.p. °C. | Percent Yield | Percent C Calc'd. | Percent C Found | Percent H Calc'd. | Percent H Found | Percent N Calc'd. | Percent N Found | Percent F Calc'd. | Percent F Found |
|---|---|---|---|---|---|---|---|---|---|---|---|---|
| 5 | A | 4-pyridyl | 239-40 | 96 | 69.83 | 69.28 | 3.59 | 3.71 | 12.49 | 12.17 | — | — |
| 6 | A | 4,6-dimethyl-2-pyridyl | 196-7[a] | 99 | 71.41 | 71.35 | 4.79 | 4.81 | 11.10 | 11.07 | — | — |
| 6 | A | 3,5-dichloro-2-pyridyl | 173[b] | 84 | 53.27 | 53.43 | 2.06 | 1.96 | 9.56 | 9.70 | 24.19 | 23.92 |
| 8 | A | 2-methoxy-3-pyridyl | 275-6[c] | Theor. | 66.14 | 66.29 | 3.96 | 4.06 | 11.02 | 11.23 | — | — |
| 9 | B | 4-methylphenyl | 210-11[d] | 99 | — | — | — | — | 5.90 | 5.75 | — | — |
| 10 | B | 4-mercaptophenyl | 161-2[d] | Theor. | — | — | — | — | 5.49 | 5.34 | (e) | (e) |
| 11 | B | 4-fluorophenyl | 192-3[d] | 97 | — | — | — | — | 5.81 | 5.72 | 7.88 | 7.95 |
| 12 | B | 4-(carboxymethylthio)phenyl | 211-12 | 94 | — | — | — | — | 4.47 | 4.57 | (f) | (f) |
| 13 | B | 3-methoxy-4-trifluoromethylphenyl | 194-5 | Theor. | 59.82 | 60.04 | 3.14 | 3.04 | 4.36 | 4.49 | 17.74 | 17.54 |
| 14 | B | 4-bromo-3-methylphenyl | 195-6[g] | 88 | 51.38 | 51.64 | 2.59 | 2.42 | 4.00 | 3.81 | — | — |
| 15 | B | 4-(1-hydroxyethyl)phenyl (CH₃—CHOH substituted phenyl with Cl) | 100-1[a] | 96 | 71.90 | 71.87 | 4.90 | 5.10 | 5.24 | 5.01 | — | — |
| 16 | B | 4-chloro-3-trifluoromethylphenyl | 173[g] | 92 | 55.32 | 55.40 | 2.17 | 2.13 | 4.32 | 4.29 | — | — |
| 17 | C | 3-chloro-4-trifluoromethylphenyl | 122-3[a] | 94 | 55.32 | 55.13 | 2.17 | 2.10 | 4.30 | 4.23 | — | — |

-continued

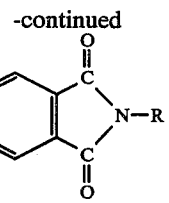

| Ex. # | Procedure | R | m.p. °C. | Percent Yield | Percent C Calc'd. | Percent C Found | Percent H Calc'd. | Percent H Found | Percent N Calc'd. | Percent N Found | Percent F Calc'd. | Percent F Found |
|---|---|---|---|---|---|---|---|---|---|---|---|---|
| 18 | C | —CH₂—C₆H₃(CF₃)(Cl) | 154-5(h) | 99 | 55.32 | 55.31 | 2.17 | 2.17 | 4.30 | 4.27 | — | — |
| 19 | C | —CH₂—pyridyl-Cl | 153-4(i) | 79 | — | — | — | — | 10.83 | 10.74 | 13.71 | 13.61 |
| 20 | C | —CH₂—C₆H₃(Cl)(Cl) | 206-7(d) | 97 | 57.56 | 56.62 | 2.42 | 2.45 | 4.80 | 4.77 | 24.28 | 24.39 |
| 21 | C | —CH₂—C₆H₄—Cl | 202-3(d) | 99 | 65.46 | 65.61 | 3.13 | 2.92 | — | — | — | — |

(a)Recrystallization from isopropyl alcohol.
(b)Recrystallization from toluene.
(c)Recrystallization from DMF.
(d)Recrystallization from ethyl acetate.
(e)Calc'd.: S, 12.56; Found: S, 12.52.
(f)Calc'd.: S, 10.23; Found: S, 10.07.
(g)Recrystallization from isopropyl alcohol - ethyl acetate.
(h)Recrystallization from heptane - isopropyl alcohol.
(i)Recrystallization from methyl alcohol.

Compounds 22-26 have been prepared as follows:

Preparation of Compound 22

To a stirred slurry containing 18.6 grams (0.1 moles) of potassium salt of phthalimide and 150 ml of DMF, 14.5 grams (0.1 moles) of m-fluorobenzyl chloride is added in one portion. The stirred reaction mixture is heated at 110°-120° C. for 6 hours and at 25°-30° C. for 18 hours. After the addition of 800 ml of water, the reaction mixture is stirred at 0°-10° C. for one hour. The solid is collected by filtration, washed with water until neutral to litmus and air-dried at 25°-30° C. The product, m.p. 139°-140° C., is obtained in 94% yield. After recrystallization from isopropyl alcohol, it melted at 141°-142° C.

Anal. Calc'd. for $C_{15}H_{10}FNO_2$: N, 5.49; F, 7.44. Found: N, 5.35; F, 7.31.

Preparation of Compound 23

To a stirred slurry containing 22.1 grams (0.15 moles) of phthalimide and 260 ml of isopropyl alcohol, 15 ml of 37% aqueous formaldehyde is added in one portion. After heating to reflux, 16.7 grams (0.15 moles) of p-fluoroaniline is added in one portion and stirring continued at reflux for one hour. After cooling to 5° C., 300 ml of petroleum ether is added and stirring continued at 0°-10° C. for one hour. The solid is collected by filtration and air-dried at 25°-30° C. The product, m.p. 173°-174° C., is obtained in 94% yield. After recrystallization from ethyl acetate, it melted at 174°-175° C.

Anal. Calc'd. for $C_{15}H_{11}FN_2O_2$: N, 10.37; F, 7.03. Found: N, 10.26; F, 7.06.

Preparation of Compound 24

To a stirred solution containing 22.1 grams (0.2 moles) of thiophenol, 13.2 grams of 85% potassium hydroxide, 200 ml of acetone and 10 ml of water, 35.4 grams (0.18 moles) of N-(chloromethyl)phthalimide is added in one portion. An exothermic reaction set in causing a temperature rise from 28°-49° C. After stirring for one hour, 700 ml of ice water is added. The solid is collected by filtration, washed with water until neutral to litmus and air-dried at 25°-30° C. The product, m.p. 126°-128° C., is obtained in 87% yield. After recrystallization from heptane, it melted at 133°-134° C.

Anal. Calc'd. for $C_{15}H_{11}NO_2S$: N, 5.20; S, 11.91. Found: N, 5.24; S, 11.87.

Preparation of Compound 25

To a stirred slurry containing 23.9 grams (0.1 moles) of N-(m-hydroxyphenyl)phthalimide, 400 ml of acetone and 1 ml of triethylamine, 6.3 grams (0.11 moles) of methylisocyanate is added in one portion. After heating at reflux for one hour, the stirred reaction mixture is cooled to 5° C. After stirring at 0°-10° C. for 30 minutes, the solid is collected by filtration and air-dried at 25°-30° C. The product, m.p. 179°-181° C., was obtained in 98% yield. After recrystallization from acetone, it melted at 190°-191° C.

Anal. Calc'd. for $C_{16}H_{12}N_2O_4$: C, 64.86; H, 4.08; N, 9.46. Found: C, 64.91; H, 4.16; N, 9.31.

Preparation of Compound 26

To a stirred slurry containing 40.8 grams (0.22 moles) of potassium salt of phthalimide and 200 ml DMF, 45.2 grams (0.2 moles) of 4-chloro-3-nitro-benzotrifluoride is added in one portion and heated at 90°-100° C. for 24 hours. After cooling to 0° C., 800 grams of ice water is added and stirring continued at 0°-10° C. for one hour. The solid is collected by filtration, washed with water until neutral to litmus and air-dried at 25°-30° C. The product, m.p. 183°-185° C., is obtained in 97% yield. After recrystallization from isopropyl alcohol, it melted at 192°-193° C.

Anal. Calc'd. for $C_{15}H_7F_3N_2O_4$: C, 53.58; H, 2.10; F, 16.95; N, 8.33. Found: C, 53.70; H, 1.99; F, 17.11; N, 8.31.

Compounds 1-26 have been found to be effective in altering the development of reproductive components of corn plants. As used herein, the alteration of the "development of the reproductive component" of the corn plant is understood to mean the modification of the normal sequential development of said component to maturity. Such modifications are most readily observed as inhibition of tassel growth, inhibition of lateral tassel branches, alteration in ear numbers, shape, position, kernel numbers, speed of silking, etc.

The invention contemplates the alteration of the development of the reproductive components of healthy corn plants by applying an effective, non-lethal amount of the active ingredient to said corn plant before or during the early stages of the development of said reproductive component referred to herein as reproductive differentiation. As a result of such application, tassel size can be reduced or eliminated, thus reducing or eliminating the labor required by hybrid seed corn producers to manually detassel said corn plants. Additionally, the amount of seed per unit area of land may be increased by applying an effective amount of the active ingredient before or during the early stages of the development of said ear.

As used herein, the term "active ingredient" refers to compounds 1-26 above.

In accordance with the novel aspects of the present invention, compounds 1-26 were tested in accordance with the following procedure:

Example A

A-619 variety corn plants were grown and thinned to obtain a uniform population. All weak or late plants were removed before chemical application. The active ingredient was formulated by adding 50 or 100 mg of the active ingredient to 7.5 ml of acetone and 7.5 ml of water. 0.25% Tween 20 was added as a surfactant. Utilizing a Devilbiss #152 sprayer, the corn plants were sprayed during the early stages of reproductive differentiation at a rate of 10 mg per plant or 20 mg per plant.

Results were analyzed by comparing the treated plants to control plants which were not chemically treated. Chemicals were considered to be active in altering the reproductive development of the corn plant if treatment resulted in an inhibition of at least 25% of the lateral tassel formation when compared to the control plants.

In accordance with the above procedure, compounds 1, 2, 6, 7, 13, 16, 18, 19 and 21 were found to be effective in inhibiting from 50 to 74% of the lateral tassel development. The remaining compounds were found to be effective in inhibiting from 25 to 49% of the lateral tassel development. In addition, flowering was inhibited as illustrated in Table II.

Table II

| Compound | cm. of Flowers |
|---|---|
| Control | 224 |
| 1 | 188 |
| 2 | 83 |
| 6 | 167 |
| 16 | 195 |
| 13 | 194 |
| 18 | 126 |
| 19 | 163 |

Example B

Pioneer 3369A variety corn plants were grown and treated with 5 or 10 mg per plant of the active ingredient dissolved in acetone and a surfactant. Treatments were applied either 5 days, 8 days or 12 days after plant emergence. Ten plants were utilized for the test. At harvest, the position of the primary ear was noted and expressed as a ratio of ear height to plant height. Comparisons with untreated control plants are noted in Table III, below.

Table III

| Compound | Date of Application Days after Emergence | Rate mg/plant 0 | 5 | 10 |
|---|---|---|---|---|
| 1 | 5 | .466 | .560 | .505 |
|  | 8 | .511 | .518 | .501 |
|  | 12 | .503 | .505 | .498 |
| 2 | 5 | .479 | .478 | .485 |
|  | 8 | .479 | .539 | .509 |
|  | 12 | .479 | .474 | .458 |
| 13 | 5 | .540 | .503 | .485 |
|  | 8 | .542 | .504 | .513 |
|  | 12 | .500 | .504 | .513 |
| 16 | 5 | .518 | .529 | .516 |
|  | 8 | .554 | .517 | .495 |
|  | 12 | .491 | .543 | .526 |
| 18 | 5 | .490 | .543 | .500 |
|  | 8 | .492 | .494 | .473 |
|  | 12 | .501 | .494 | .514 |
| 19 | 5 | .497 | .497 | .470 |
|  | 8 | .490 | .508 | .483 |
|  | 12 | .489 | .533 | .538 |
| 20 | 5 | .498 | .495 | .501 |
|  | 8 | .473 | .517 | .573 |
|  | 12 | .477 | .543 | .538 |
| 21 | 5 | .481 | .496 | .517 |
|  | 8 | .507 | .511 | .489 |
|  | 12 | .524 | .515 | .505 |

The above data illustrate that alteration of the position of the primary ear may be obtained by application of the active ingredient to said plants. The invention contemplates the application of the phthalimides previously described at the appropriate time during early stages of the reproductive differentiation. Reproductive differentiation occurs at different times depending upon the variety of corn plant as well as environmental factors. For example, male reproductive differentiation of Gaspé corn begins during kernal formation while reproduction differentiation of A-619 corn begins within the first 8 to 12 days after seedling emergence. The determination of when reproductive differentiation occurs is within the skill of the art. By way of example and for purposes of illustration only, applications for most varieties used in the Midwest of the United States ranging from 3 to 25 days after seedling emergence are desirable. Varieties used in foreign countries may require applications ranging from 1 to 40 days from seedling emergence.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 5 to 95 parts active ingredient, about 1 to 50 parts surface-active agent and about 4 to 94 parts solvents, all parts being by weight based on the total weight of the composition.

In selecting the appropriate rate of application of the active ingredient, it will be recognized that precise rates will also be dependent upon the mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above.

This invention, however, does not contemplate the use of phytotoxic rates which exert a herbicidal effect.

In addition, it will be recognized that single or multiple applications may be used to exert the desired response.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. A method for altering the development of the reproductive components of a corn plant which comprises applying to said corn plant an effective, non-lethal amount of a compound selected from the group consisting of:

N-(3-trifluoromethyl-4-nitrophenyl)phthalimide
N-(2-trifluoromethyl-5-bromophenyl)phthalimide
N-(3,5-dimethoxyphenyl)phthalimide
N-(3,4-dimethoxyphenyl)phthalimide
N-(4-pyridyl)phthalimide
N-(4,6-dimethyl-2-pyridyl)phthalimide
N-3,5-dichloro-2-pyridyl)phthalimide
N-(6-methoxy-3-pyridyl)phthalimide
N-(4-methylphenyl)phthalimide
N-(3-mercaptophenyl)phthalimide
N-(2-fluorophenyl)phthalimide
2-(p-phthalimidophenylthio)acetic acid
N-(3-trifluoromethyl-4-methoxyphenyl)phthalimide
N-(2-methyl-4-bromo-5-chlorophenyl)phthalimide
N-[m-(1-hydroxyethyl)phenyl]phthalimide
N-(3-trifluoromethyl-4-chlorophenyl)phthalimide
N-(2-chloro-5-trifluoromethylphenyl)phthalimide
N-(2-trifluoromethyl-4-chlorophenyl)phthalimide
N-(5-chloro-2-pyridyl)phthalimide
N-(3,5-dichlorophenyl)phthalimide
N-(4-chlorophenyl)phthalimide
N-(m-fluorobenzyl)phthalimide
N-(p-fluoroanilinomethyl)phthalimide
N-(phenylthiomethyl)phthalimide
m-phthalimidophenyl methylcarbamate
N-(2-nitro-4-trifluoromethylphenyl)phthalimide 2. The method according to claim 1 wherein said compound is applied from about 7 to about 20 days from seedling emergence.

3. The method of claim 1 wherein said reproductive component is the male component.

4. The method of claim 1 wherein said reproductive component is the female component.

* * * * *